United States Patent
Safranski et al.

(10) Patent No.: US 10,582,998 B1
(45) Date of Patent: Mar. 10, 2020

(54) SHAPE MEMORY POLYMER FABRICS

(71) Applicant: MedShape, Inc., Atlanta, GA (US)

(72) Inventors: David Safranski, Atlanta, GA (US);
Kathryn Smith, Atlanta, GA (US);
Jack C. Griffis, III, Decatur, GA (US)

(73) Assignee: MEDSHAPE, INC., Atlanta, GA (US)

( * ) Notice: Subject to any disclaimer, the term of this patent is extended or adjusted under 35 U.S.C. 154(b) by 472 days.

(21) Appl. No.: 13/654,193

(22) Filed: Oct. 17, 2012

(51) Int. Cl.
*A61F 2/08* (2006.01)

(52) U.S. Cl.
CPC ........................................ *A61F 2/08* (2013.01)

(58) Field of Classification Search
CPC ...... A61F 2/86; A61F 2/90; A61F 2/91; A61F 2/915; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2/0063; A61F 2002/0068; A61F 2/08; A61F 2/0811; A61F 2002/0847; A61F 2/28; A61F 2/2803; A61F 2002/2817; A61F 2002/2835; A61F 2/2846; A61F 2002/285

See application file for complete search history.

(56) References Cited

U.S. PATENT DOCUMENTS

| | | | | |
|---|---|---|---|---|
| 5,674,242 A * | 10/1997 | Phan | ........................ | A61F 2/07 606/195 |
| 6,500,204 B1 * | 12/2002 | Igaki | ........................ | A61F 2/90 623/1.18 |
| 7,824,601 B1 * | 11/2010 | Stankus | ................... | A61L 31/14 264/131 |
| 9,078,738 B2 * | 7/2015 | Wilson | ............. | A61B 17/12022 |
| 10,052,218 B2 * | 8/2018 | Winshtein | ................. | A61F 2/95 |
| 2001/0047202 A1 * | 11/2001 | Slaikeu | ............ | A61B 17/12022 623/1.46 |
| 2002/0045931 A1 * | 4/2002 | Sogard | ...................... | A61F 2/07 623/1.13 |
| 2002/0058985 A1 * | 5/2002 | DePalma | ................ | A61F 2/064 623/1.13 |
| 2002/0084178 A1 * | 7/2002 | Dubson | ..................... | A61F 2/06 204/157.6 |

(Continued)

OTHER PUBLICATIONS

Merriam-Webster definition for "rectangle" accessed Apr. 30, 2019; https://www.merriam-webster.com/dictionary/rectangle.*

*Primary Examiner* — Wade Miles
(74) *Attorney, Agent, or Firm* — Morris, Manning & Martin, LLP; Bryan D. Stewart

(57) ABSTRACT

The disclosure describes a method including manufacturing a shape memory polymer fabric with a collection of shape memory polymer fibers such that the resulting shape memory polymer fabric has a glass transition temperature of greater than 50 degrees centigrade. The method further includes training the shape memory polymer fabric with a pre-determined percentage of strain between an expanded shape and a contracted shape. The method further includes preparing a portion of the shape memory polymer fabric into a shape that is sized to cover two portions of a ruptured soft tissue of an animal with a mean body temperature below 40 degrees centigrade while the fabric has the predetermined percentage of strain stored in the expanded shape.

9 Claims, 7 Drawing Sheets

(56) References Cited

U.S. PATENT DOCUMENTS

| | | | |
|---|---|---|---|
| 2003/0216804 A1* | 11/2003 | DeBeer | A61F 2/90 623/1.15 |
| 2004/0037813 A1* | 2/2004 | Simpson | A61F 2/08 424/93.7 |
| 2004/0098090 A1* | 5/2004 | Williams | A61F 2/91 623/1.13 |
| 2005/0113938 A1* | 5/2005 | Jamiolkowski | A61F 2/08 623/23.74 |
| 2005/0152938 A1* | 7/2005 | Williams | A61F 2/90 424/423 |
| 2005/0187605 A1* | 8/2005 | Greenhalgh | A61F 2/07 623/1.15 |
| 2005/0202067 A1* | 9/2005 | Lendlein | A61F 2/0063 424/443 |
| 2005/0267570 A1* | 12/2005 | Shadduck | A61B 17/12022 623/1.44 |
| 2006/0271093 A1* | 11/2006 | Holman | A61F 2/958 606/194 |
| 2007/0026132 A1* | 2/2007 | Williams | A61F 2/90 427/2.25 |
| 2007/0142907 A1* | 6/2007 | Moaddeb | A61F 2/2418 623/2.11 |
| 2007/0207186 A1* | 9/2007 | Scanlon | A61F 2/07 424/424 |
| 2007/0208373 A1* | 9/2007 | Zaver | A61F 2/06 606/200 |
| 2007/0219642 A1* | 9/2007 | Richter | A61F 2/91 623/23.7 |
| 2007/0255392 A1* | 11/2007 | Johnson | A61F 2/92 623/1.15 |
| 2007/0293927 A1* | 12/2007 | Frank | A61F 2/90 623/1.11 |
| 2008/0091222 A1* | 4/2008 | Deusch | A61F 2/0063 606/151 |
| 2008/0300668 A1* | 12/2008 | Bonsignore | A61F 2/91 623/1.15 |
| 2009/0005760 A1* | 1/2009 | Cartledge | A61F 2/07 604/534 |
| 2009/0187240 A1* | 7/2009 | Clerc | A61L 31/10 623/1.17 |
| 2009/0248141 A1* | 10/2009 | Shandas | A61B 17/12022 623/1.19 |
| 2010/0104849 A1* | 4/2010 | Lashmore | A61F 2/91 428/305.5 |
| 2010/0189764 A1* | 7/2010 | Thomas | A61F 2/0063 424/426 |
| 2010/0292791 A1* | 11/2010 | Lu | A61K 38/18 623/13.12 |
| 2011/0230955 A1* | 9/2011 | Orion | A61F 2/82 623/1.15 |
| 2011/0250689 A1* | 10/2011 | Baaijens | D01D 5/0076 435/398 |
| 2012/0035524 A1* | 2/2012 | Silvestrini | A61F 2/90 604/8 |
| 2012/0232643 A1* | 9/2012 | Ramzipoor | A61L 31/148 623/1.15 |
| 2013/0173017 A1* | 7/2013 | McHugo | A61F 2/88 623/23.69 |
| 2013/0197623 A1* | 8/2013 | McHugo | A61F 2/852 623/1.18 |
| 2013/0218178 A1* | 8/2013 | Shandas | A61F 2/0063 606/151 |
| 2014/0052234 A1* | 2/2014 | Winshtein | A61F 2/06 623/1.11 |
| 2014/0081386 A1* | 3/2014 | Haselby | A61F 2/07 623/1.46 |

* cited by examiner

| | Mean Fiber Diameter (um) | Glass Transition Temperature (deg. C) (tan-delta) |
|---|---|---|
| Exemplary Embodiment 1 | 9.11 +/- 2.03 | 65 +/- 3.4 |
| Exemplary Embodiment 2 | 5.56 +/- 2.28 | 65.6 +/- 2 |
| Exemplary Embodiment 3 | 9.06 +/- 2.01 | 60.3 +/- 2.5 |
| Exemplary Embodiment 4 | 7.89 +/- 1.47 | 65 +/- 2.6 |
| Exemplary Embodiment 5 | 5.33 +/- 1.63 | 63.3 +/- 4 |
| Exemplary Embodiment 6 | 5.5 +/- 1.62 | 62.6 +/- 5.1 |
| Exemplary Embodiment 7 | 4.09 +/- 1.18 | 65 +/- 4 |
| Exemplary Embodiment 8 | 5.8 +/- 1.83 | 60 +/- 4.3 |
| Exemplary Embodiment 9 | 9.07 +/- 2.22 | 54.6 +/- 3.7 |

FIG. 7

SHAPE MEMORY POLYMER FABRICS

FIELD OF THE TECHNOLOGY

Embodiments of this disclosure relate to shape memory polymer fabrics and configurations thereof.

BACKGROUND

Shape memory polymers provide the ability to store strain in an installed or "temporary" shape via a shape memory effect, whereby the stored strain may be recovered by the shape memory polymer to an "unconstrained" shape, memorized, or original shape via heating or otherwise activating the shape memory polymer.

SUMMARY OF THE DESCRIPTION

Provided herein are shape memory fabrics including polymers with transition temperatures above their intended temperatures of use.

In one aspect, the disclosure describes a shape memory polymer fabric including a collection of shape memory polymer fibers, the collection exhibiting a storage temperature below 40 degrees centigrade and a glass transition temperature at or above 50 degrees centigrade. The shape memory polymer fabric has a stored strain defining a difference in length of an active dimension of the fabric. The difference in length defining a difference between an installed shape and an unconstrained shape, thereby causing the unconstrained shape to differ by more than a soft tissue rupture distance.

In another aspect, the disclosure describes a method including manufacturing a shape memory polymer fabric with a collection of shape memory polymer fibers such that the resulting shape memory polymer fabric has a glass transition temperature of greater than 50 degrees centigrade. The method further includes training the shape memory polymer fabric with a pre-determined percentage of strain between an expanded shape and a contracted shape. The method further includes preparing a portion of the shape memory polymer fabric into a shape that is sized to cover two portions of a ruptured soft tissue of an animal (e.g., a tendon) with a mean body temperature below 40 degrees centigrade while the fabric has the predetermined percentage of strain stored in the expanded shape. The method further includes packaging the shape memory polymer fabric in a sterile medical package for storage in the expanded shape.

In some embodiments, the method includes sterilizing the fabric in a manner that leaves the fabric below an activation temperature of the fabric, thereby inducing no recovery of the stored strain during the sterilizing step. In some embodiments, the collection of shape memory polymer fibers are interlaced with each other in a periodic array. In some embodiments, the periodic array comprises a weave pattern with a plurality of orthogonal fiber directions. In some embodiments, the collection of shape memory polymer fibers form a non-woven mesh with varying degrees of shape memory polymer fiber entanglement.

Other embodiments and features of the present disclosure will be apparent from the accompanying drawings and from the detailed description which follows.

BRIEF DESCRIPTION OF THE DRAWINGS

The embodiments are illustrated by way of example and not limitation in the Figures of the accompanying drawings in which like references indicate similar elements.

FIG. 7 shows processing data for other exemplary embodiments of non-woven shape memory polymer fabrics.

Woven patterns illustrations shown are attributed to Juancourt (2007).

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one. Reference in this specification to "one embodiment" or "an embodiment" or the like means that a particular feature, structure, or characteristic described in connection with the embodiment is included in at least one embodiment of the disclosure. The appearances of the phrase "in one embodiment" or the like in various places in the specification are not necessarily all referring to the same embodiment, nor are separate or alternative embodiments mutually exclusive of other embodiments. Moreover, various features are described that may be exhibited by some embodiments and not by others.

Figure 1:
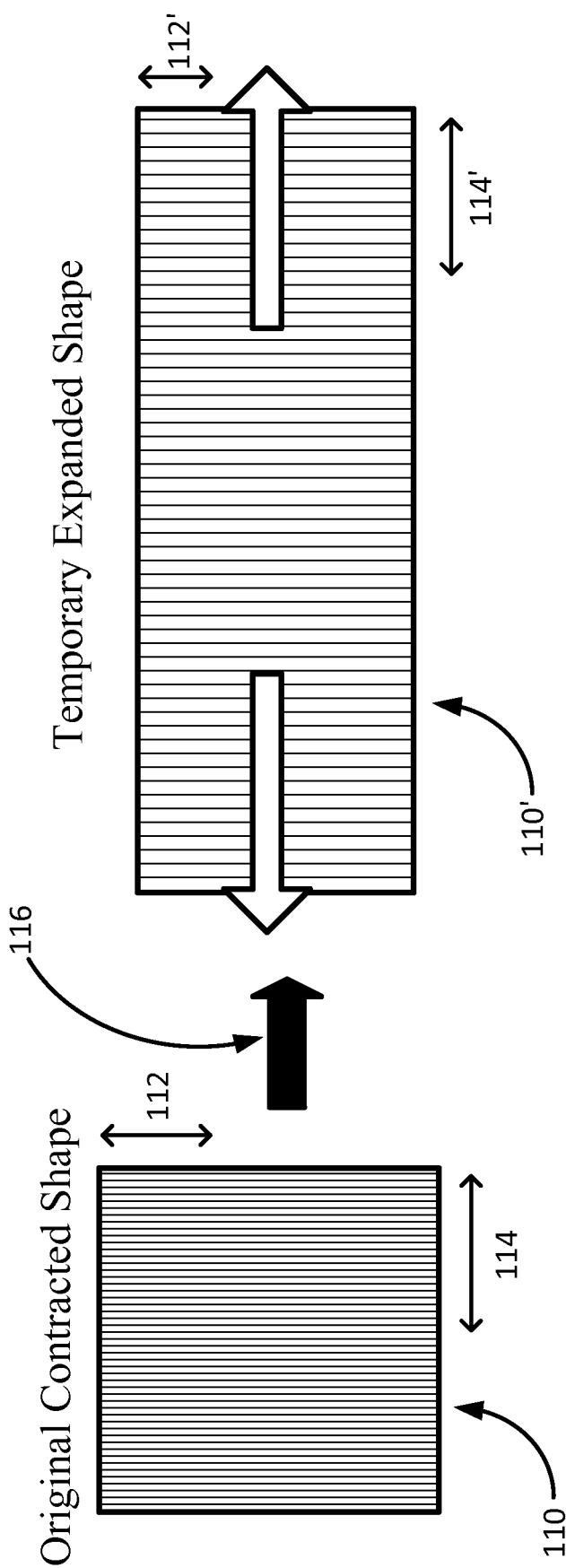
FIG. 1 illustrates an exemplary embodiment a shape memory polymer fabric illustrating an original contracted shape and stretching it into a temporary expanded shape.

FIG. 1 illustrates an exemplary embodiment a shape memory polymer fabric illustrating an original contracted shape 110 and stretching it into a temporary expanded shape 110'. The original contracted shape 110 is also referred to herein as the "unconstrained shape" because the fabric is will recover toward over time, as described further herein. The unconstrained shape may not be reached due to stresses or constraints applied to the fabric, such as by the tendon(s) or bone(s) to which the fabric is attached. The original contracted shape 110 may be formed by conventional means, namely sizing the fabric to the unconstrained shape (or original contracted shape) without any stored strain in the shape memory polymer fabric. In other words, heating the fabric in the unconstrained shape to its glass transition temperature (and above) causes no recovery of any stored strain in the fabric. The temporary expanded shape 110' is then created by stretching the fabric 116 along one or more axes, such as along original lateral dimension 114 to temporary expanded lateral dimension 114'. The temporary expanded shape 110' is also referred to herein as the "installed shape" because the fabric is intended to be installed in the body in this shape before activation and recovery of the stored strain back toward the unconstrained or original shape 110. After stretching 116 in the lateral dimension 114, the temporary expanded lateral dimension 114' is held while cooling the shape memory polymer fabric 110' below the glass transition temperature. Alternatively, in other embodiments, the shape memory polymer fabric in its unconstrained shape 110 may be stretched 116 or otherwise deformed (e.g., stretched on more than one axis), and the stored strain may be imparted and set, while the fabric remains at or below the glass transition temperature.

In one embodiment, the shape memory polymer fabric is sized to cover a tissue rupture site in an animal. For example, the shape memory polymer fabric may be formed in the original contracted shape 110 to span or cover a soft tissue (e.g., tendon) rupture distance, such as for a rotator cuff augmentation surgical procedure. In the exemplary rotator cuff augmentation technique, an active dimension 114 of the fabric is installed along a medial-lateral dimension of the body to span the soft tissue rupture, and moderated long-term activation of the fabric provides sustained tension across the soft tissue rupture, advantageously decreasing related muscle atrophy and fatty infiltration of affected soft tissues. In alternate embodiments, a soft tissue rupture distance may be measured or determined from or across a ruptured tendon interface, such as from tendon to tendon, or from tendon to bone, or a combination thereof. A difference in length of the active dimension of the fabric 114, as shown between original active dimension 114 and, after stretching 116, the stretched active dimension 114' may be related to the soft tissue rupture distance through sizing during surgery (e.g., at a surgical preparation table) based on this measured distance. As described further herein, the difference in length along the active dimension 114 may be determined as a unit distance or as a percentage of stored strain to facilitate easy sizing during surgery.

In one embodiment, the soft tissue rupture is intended to be measured during surgery and the fabric sized during surgery (e.g., at a back table) after a stored strain is stored in the fabric in one or more active dimensions 114 of the fabric. Therefore, one embodiment of the fabric includes a predetermined percentage of stored strain, such that the fabric is monotonic in terms of shape memory response along the active dimension, such as the lateral dimension 114 and 114' of the fabric. For example, engineering strains of 55%-225% may be imparted along the active dimension (e.g., original active dimension 114) through the training process. As described further herein, the stored strain may be imparted to (or "trained" into) the SMP fabric at a training temperature, which may be above or below the respective the glass transition temperatures of the SMP fabrics described herein.

In one embodiment, the original contracted shape 110 includes a lateral dimension 114 that is related to the soft tissue rupture distance. The soft tissue rupture distance may be measured and the size of the fabric determined, as further described herein, such that activation of the fabric over time in the body will provide consistent forces over a therapeutic period of time, such as 1-6 months. In one embodiment, the stored strain in the fabric provides continued tension for a period of at least 2 months. The shape memory polymer fabric may recover 90% of the stored strain, even when recovery is doubly limited by both the higher glass transition temperature and the tension opposing recovery across the fabric in the active direction. For example, after installation of the fabric the soft tissue rupture will provide active and dynamic tension across the soft tissue rupture which will counteract the fabric's recovery along the fabric's active dimension.

An active intraoperative tension of the supraspinatus tendon falls in the range of 0.12-0.42 MPa. In the same embodiment, strain recovery over time without constraint (or, free strain recovery) occurs even with a bias as great as 0.42 MPa (or partial constraint recovery), or the exemplary upper range for active intraoperative tension in the supraspinatus tendon. In one embodiment, the fabric is able to recover 2.5% of its stored strain within one hour at 37 degrees centigrade. Thus, without temperature-assisted activation, embodiments of the shape memory polymer fabric may provide sustained long-term tension across soft tissue ruptures for periods of times including months. For example, activation of the fabric may occur at an insubstantial rate for a period exceeding two months following surgery, and the stresses and recovered strains along the active dimension of the fabric caused thereby may provide continued tensions across the ruptured soft tissue interface for a similar period of time.

Sterilization of the fabric must not activate the stored strain to recover, thus sterilizing of the fabric is performed such that the fabric stays below the activation temperature such that no recovery of the stored strain is induced, which may occur before or after packaging the fabric in its expanded shape for continued storage in its expanded shape.

In one embodiment, the shape memory polymer fabric is formed (e.g., woven) such that the original vertical dimension 112 contracts to a shorter temporary vertical dimension 112' as is shown in FIG. 1, when the original lateral dimension 114 is stretched 116 to the expanded lateral dimension 114'. In another embodiment, the original vertical dimension 112 stays constant to a similar temporary vertical dimension 112' when the original lateral dimension 114 is stretched 116 to the expanded lateral dimension 114'. For example, a woven shape memory polymer fabric may be stretched 116 to expand the original lateral dimension 114, but, in one embodiment, such stretching does not commensurately change the original vertical dimension 112.

The shape memory polymer fabric may respond with a similar shape memory effect as a bulk shape memory polymer with the same dimensions, despite the shape memory polymer advantageously being formed as a woven fabric (e.g., fibers interlaced in a periodic array) or a non-woven fabric. For example, as described further herein, the shape memory polymer fabric may provide contracting forces upon activation of the shape memory polymer effects of the fabric. As described herein, the contracting forces may be tailored for installation within an animal during a surgical procedure without significant activation. For therapeutic purposes, the contracting forces may be desired to be applied by the fabric over a period of months after the surgical procedure.

The shape memory polymer fabric from the original contracted shape 110 may be stretched 116 or have a strain imparted in more than one direction when compared with the original contracted shape. In other words, in addition to or counter acting any action of the weave pattern of the shape memory polymer fabric, strain stored by the shape memory effect of the fabric may be imparted both in the temporary vertical dimension 112' and in the temporary expanded lateral dimension 114'. For example, the temporary expanded shape may comprise a stored strain in two orthogonal directions. The strain stored by shape memory effect of the fabric is stored within the fibers and may be combined with weaving effects to create a combined stress/strain relationship of the fabric.

Figure 2:
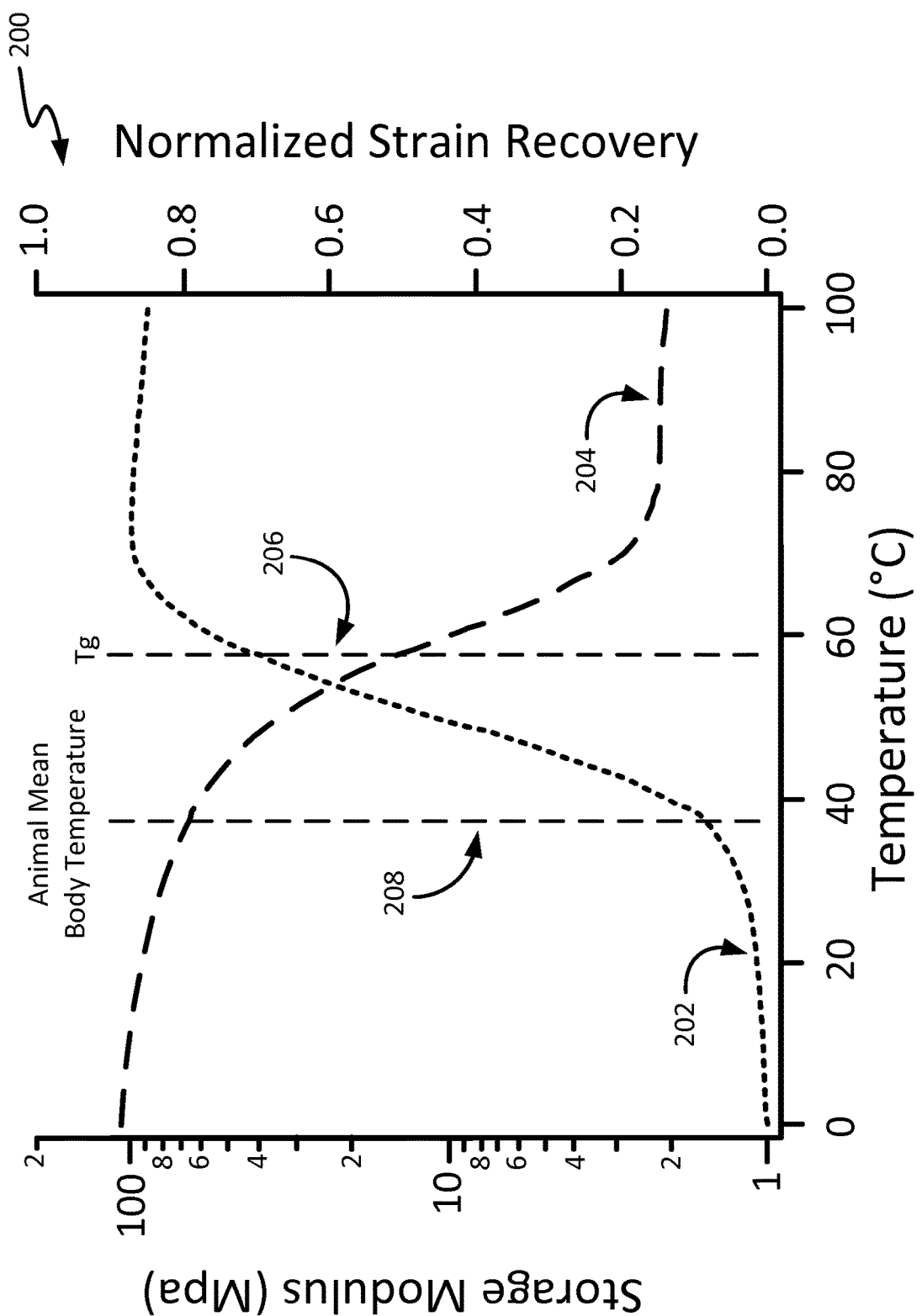
FIG. 2 shows a graph of storage modulus data and normalized strain recovery data for an exemplary embodiment of a shape memory polymer used herein.

FIG. 2 shows a graph of storage modulus data and normalized strain recovery data 200 for an exemplary embodiment of a shape memory polymer used herein. The normalized strain recovery graph line 202 shows normalized free-strain recovery, namely recovery of the strain stored by shape memory in the polymer while the polymer is heated through a range of temperatures. The storage modulus graph line 204 shows the engineering modulus (e.g., Young's modulus) of the shape memory polymer while the polymer is heated through the same range of temperatures. The glass transition temperature (Tg) 206 is determined as the peak tan-delta of the storage modulus line 204, as commonly defined using DMA analysis. The mean body temperature 208 for an animal targeted for the surgical procedure using the shape memory polymer fabric is shown below 40 degrees Celsius. For example, a human has a mean body temperature of roughly 37 degree Celsius.

The shape memory polymer is chosen with a glass transition temperature 206 that is greater than the animal's mean body temperature 208, in order that activation of the shape memory polymer will not occur or will occur only to a minimal extent or an insignificant extent during a surgical procedure. The shape memory polymer will only be insignificantly activated during the installation procedure because the body heat of the animal cannot activate the shape memory polymer on the timeframe of the surgical procedure.

The glass transition temperature 206 is chosen significantly above the mean body temperature 208 of the animal intended for the surgical procedure. For example, for a human with a mean body temperature 208 shown at 37 degrees Celsius, the glass transition temperature 206 of 60 degrees Celsius (140 degrees Fahrenheit) represents a significant difference of 23 degrees Celsius or roughly 41 degrees Fahrenheit, and an activation temperature far beyond the temperature threshold for necrosis of human body tissue. Therefore, an installed shape memory polymer fabric, when constructed of the shape memory polymer shown, will not reach a temperature where significant activation will occur. Significant activation during a surgical procedure may be considered activation that occurs on the time scale of a surgical procedure, namely within minutes or at most hours, rather than days, months, or longer. By contrast, a shape memory polymer fabric, as described herein with a glass transition temperature 206 far above the mean body temperature of the animal 208, will not activate significantly during a surgical procedure. Instead, the timeframe for activating the shape memory polymer fabric will span 2 months or more while the shape memory polymer fabric is installed inside the animal's (e.g., human's) body. For example, the mean body temperature 208 of the animal anticipated for use with the shape memory fabric may be at a temperature for the fabric that does not produce activation, absent an activation mechanism other than temperatures or conditions surrounding. As another example, the mean body temperature may activate shape recovery in the fabric, but may do so on a time scale that extends far beyond a time scale of the surgical procedure.

In one embodiment, the shape memory polymer fabric has a storage temperature or recommended storage temperature range that is well below the glass transition temperature, namely a temperature at which the fabric will not activate when stored in packaging at that temperature for a shelf life or other significant period of time. For example, a storage temperature below 40 degrees centigrade (Celsius) or roughly 104 degrees Fahrenheit allows for transport and storage well below the glass transition temperature. In the embodiments described herein of glass transition temperatures above 60 degrees centigrade, there is a difference of 20 degrees centigrade (or 36 degrees Fahrenheit). Other intended storage temperatures may be used to create the desired temperature differences to ensure that the SMP fabric does not activate during storage.

Figure 3:
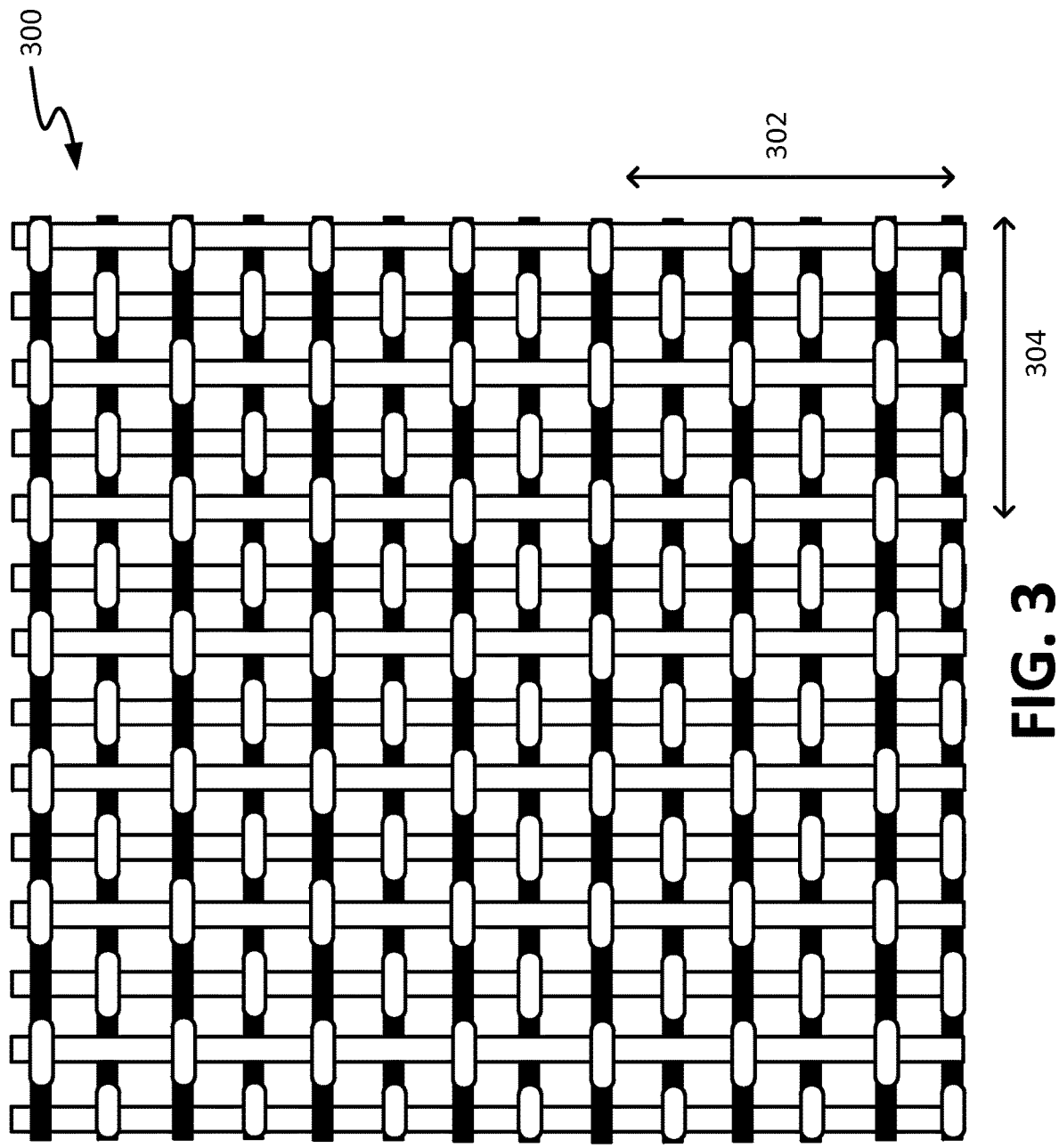
FIG. 3 shows an exemplary embodiment of a woven SMP fabric, with a plain twill weave pattern.

FIG. 3 shows an exemplary embodiment of a woven SMP fabric, with a plain twill weave pattern. The exemplary embodiment of a shape memory polymer fabric with a plain twill weave pattern 300 shows a periodic array of woven fibers with two orthogonal directions of the weave, namely the vertical direction 302 and the lateral direction 304. In order to represent the weave pattern, the image shows fibers in the lateral direction 304 as blackened when they run under fibers in the vertical direction 302. Thus, the simple twill weave pattern 300 shows one fiber in the lateral direction 304 (i.e., a warp fiber) crossing over and under fibers in the vertical direction 302 (i.e., the weft fibers), alternating for each fiber in the vertical direction.

In the descriptions herein of weaving terminology, the terms warp and weft may be construed as referring to either direction of the resulting fabric, such that any description of a particular direction of the fabric may constitute either warp or weft fibers. Other weave patterns may not include warp fibers or weft fibers as commonly defined. Terminology will be used herein that specifies a fiber direction with respect to a fabric dimension separate from whether the fibers would commonly be considered warp fibers or weft fibers. Additionally, a direction in which the fabric stores strain, namely an active dimension of the fabric, may be either the vertical direction 302 or the lateral direction 304. In some embodiments, strain may be stored in more than one direction, causing the fabric to have a plurality of active dimensions, or a composite stored strain that includes components of more than one orthogonal direction of the fabric.

In one embodiment, shape memory polymer fibers in the lateral direction 304 are the same fibers as fibers in the vertical direction 302, comprising the same shape memory polymer, with substantially the same size and treatment prior to weaving (e.g., an extrusion process). In another embodiment, fibers in the lateral direction 304 differ in some respect to the fibers in the vertical direction 302. The fibers in the vertical direction 302 and the lateral direction 304 may differ in diameter or extrusion process by which the fiber is created. For example, different extrusion techniques may make fibers with different average diameters for use in the vertical direction 302 than the lateral direction 304. In one embodiment, fibers in the vertical direction 302 and the lateral direction 304 may differ in shape memory response through varying the shape memory properties of the fibers, such as glass transition temperature. A shape memory property may be varied between the shape memory polymer fibers through varying composition, process, treatment, or training process of the different fibers. For example, different polymer compositions or processing techniques in forming the shape memory polymer fiber may create a different shape memory response for different fibers.

In one embodiment, the different shape memory properties may be imparted before weaving the different fibers into the shape memory polymer fabric. In another embodiment, the different shape memory properties may be imparted after weaving the fibers into the shape memory fabric. For example, heat treatments and strains, as described further herein, may be imparted onto the shape memory polymer fabric after it is formed in an original contracted or otherwise strain-free shape.

In one embodiment, the fibers in the vertical direction 302 and the lateral direction 304 only vary by shape memory treatment after the fibers have been woven into an orthogonal periodic array. In another embodiment, the fibers in the vertical direction 302 and the lateral direction 304 are varied in composition and/or shape memory pretreatment before weaving into a periodic array.

Figure 4:
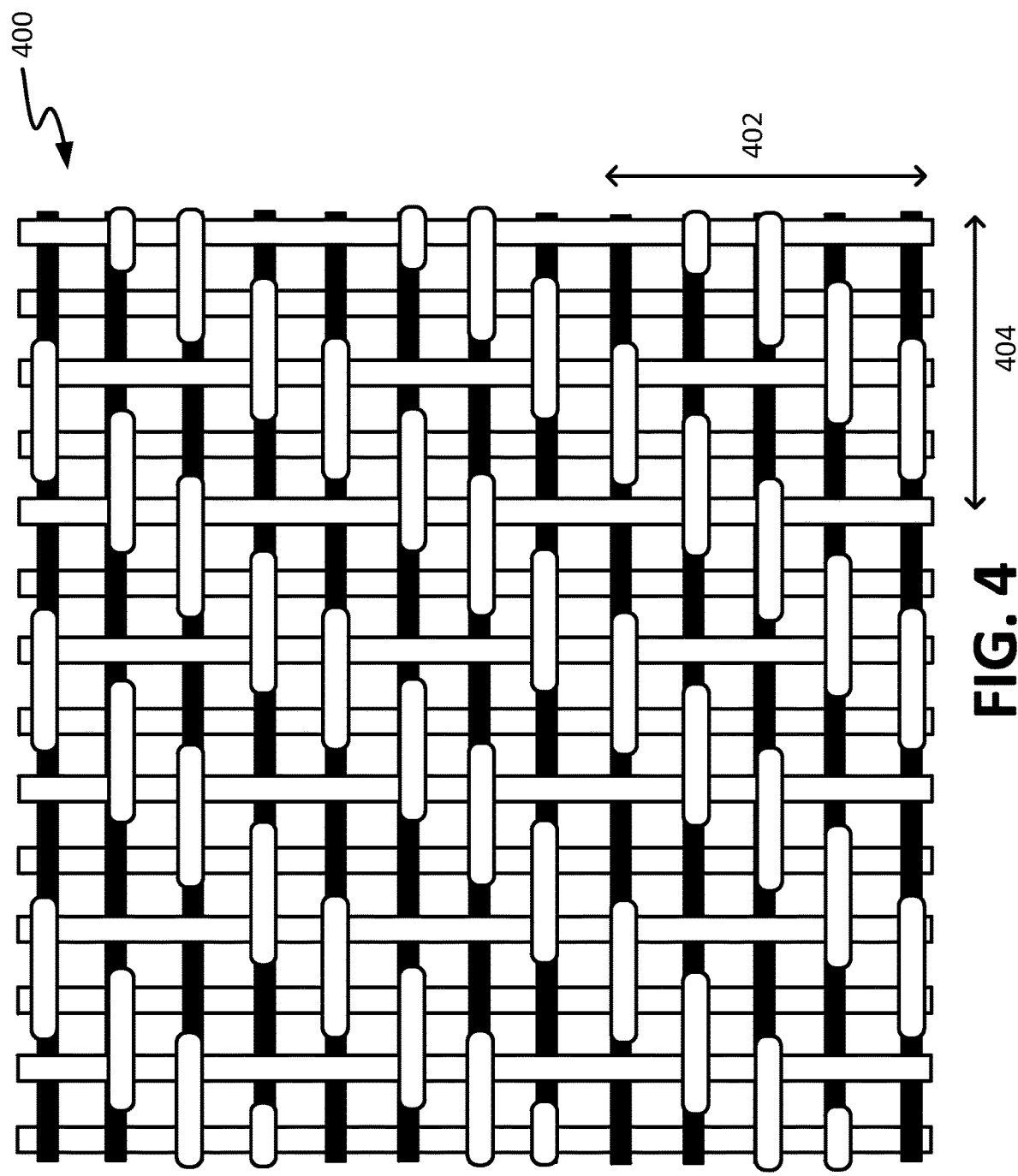
FIG. 4 shows an exemplary embodiment of a woven shape memory polymer fabric with a 2/2 twill weave pattern, including an offset.

FIG. 4 shows an exemplary embodiment of a woven shape memory polymer fabric, with a 2/2 twill weave pattern, including an offset. The exemplary 2/2 twill weave pattern in the shape memory polymer fabric includes float portions such as each fiber in the 2/2 twill pattern 400 floating over two fibers in the orthogonal direction before floating under the next two fibers in the orthogonal direction. For example, each fiber in the lateral direction 404 passes over two fibers in the vertical direction 402 before crossing under the subsequent two fibers in the vertical direction. In the embodiment shown, the point at which a fiber in the lateral direction 404 crosses from above to below the fibers in the vertical direction 402, shifts by one fiber in the vertical direction between each fiber in the lateral direction, thereby creating an offset in the 2/2 twill pattern. Other offsets and twill ratio patterns may be used and the description herein of the 2/2 twill pattern with a single offset should be considered illustrative and not limiting.

In other embodiments, other weaving patterns or periodic arrays may be used to form the shape memory polymer fabric. The twill patterns referenced herein are included for reference to the different portions of woven patterns with orthogonal fiber directions generally and not for limiting the disclosure to any of the myriad known weaving patterns. The known art in woven fabrics may be incorporated with the disclosure herein of shape memory polymer fabrics to produce heretofore unrealized synergistic gains in the treatment of soft tissue ruptures.

As described above, the fiber processing of the shape memory polymer fibers based on their position in the vertical direction 402 or the lateral direction 404. In addition, the fibers may be differently woven or otherwise include different weave patterns on different locations in the lateral direction 404 and/or the vertical direction 402 in order to synergistically cooperate with the shape memory properties of the fibers described herein.

Figure 5:
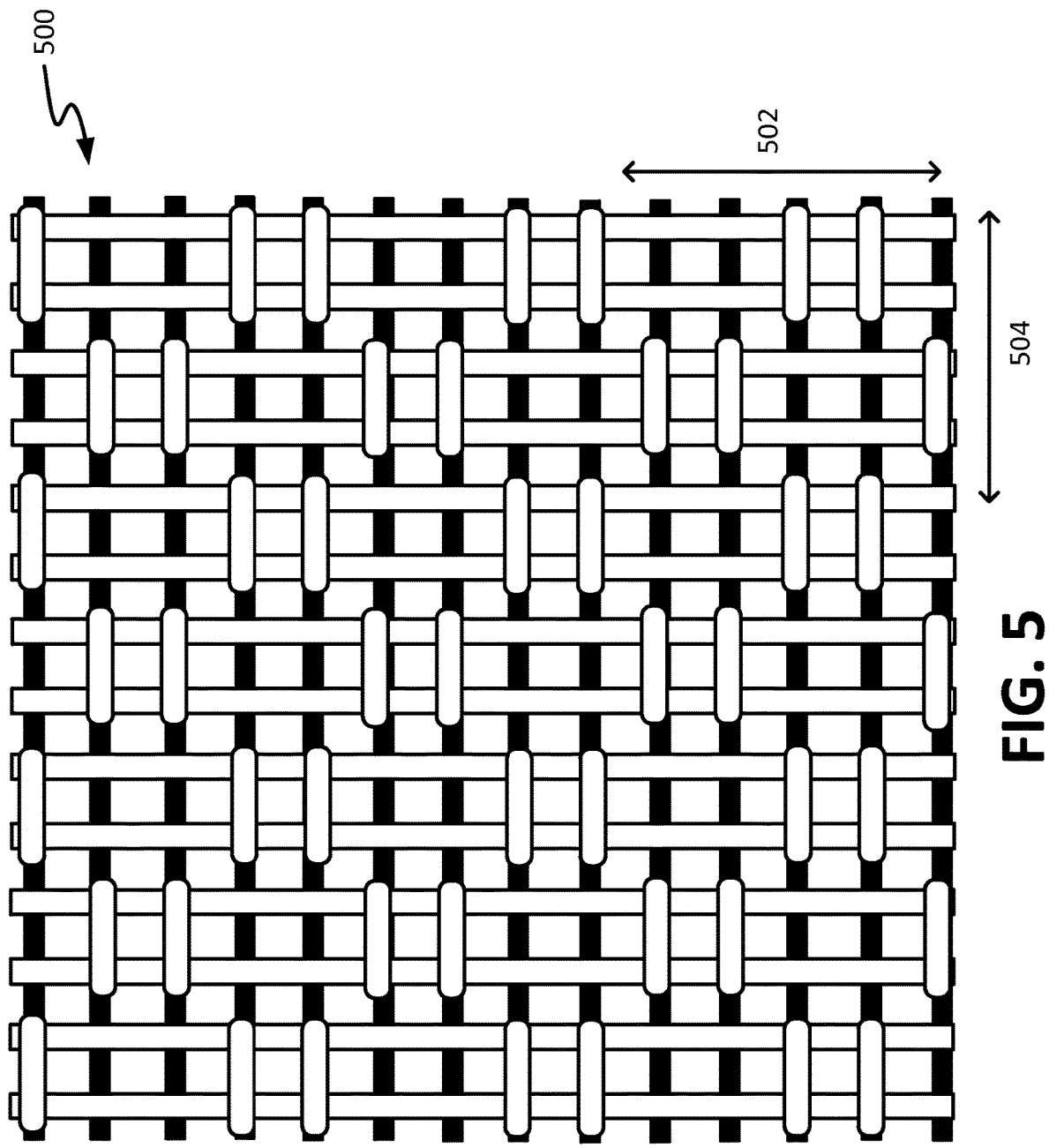
FIG. 5 shows an exemplary embodiment of a woven shape memory polymer fabric, with a 2/2 twill weave pattern, with no offset.

FIG. 5 shows an exemplary embodiment of a woven shape memory polymer fabric, with a 2/2 twill weave pattern, with no offset. In this 2/2 twill pattern with no offsets, the floats of the fibers in the vertical direction 502 are aligned and the floats of the fibers in the lateral direction 504 are aligned with each other.

Figure 6:
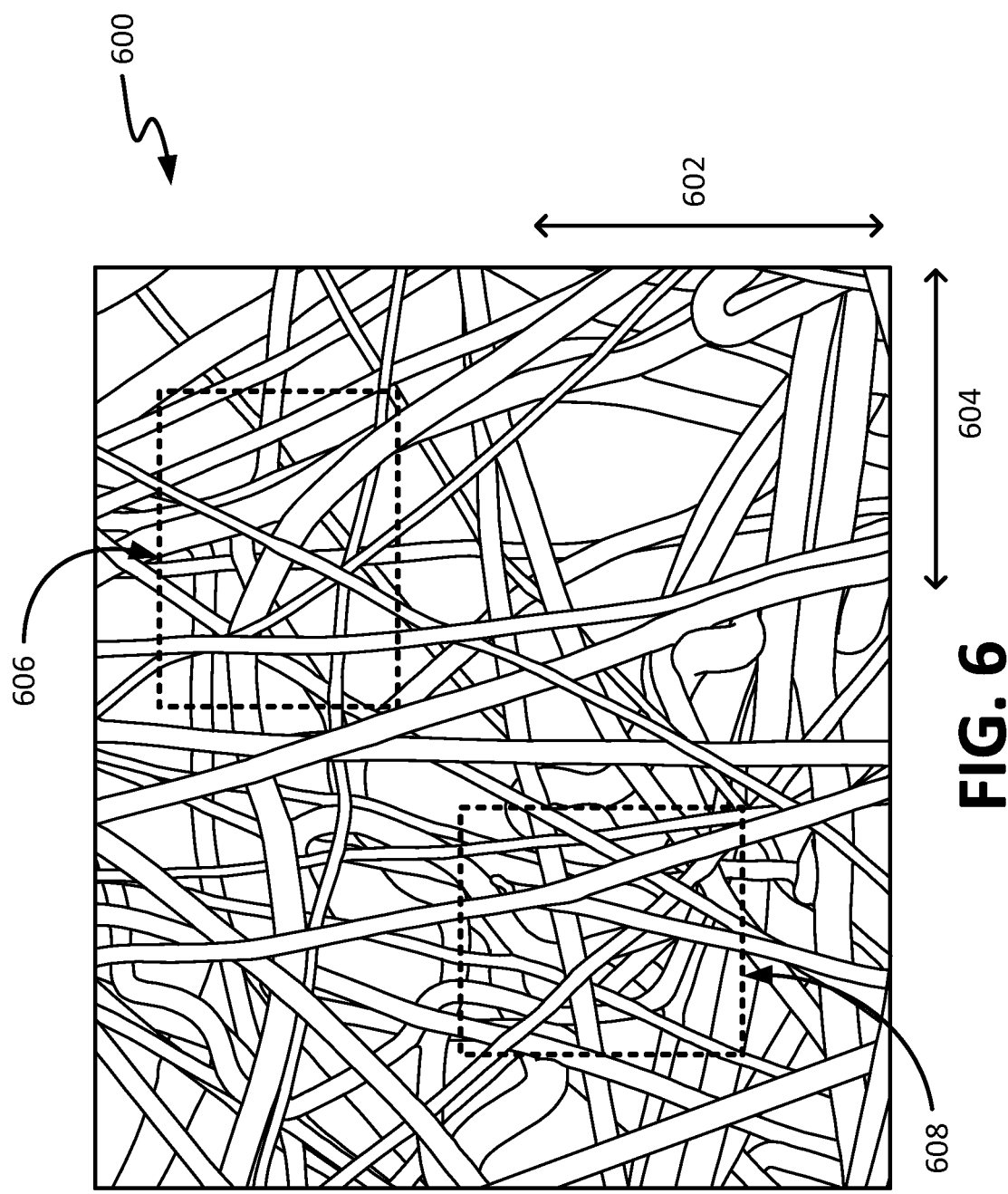
FIG. 6 shows a simplified image from a scanning electron microscope image of an exemplary embodiment of a nonwoven shape memory polymer fabric.

FIG. 6 shows a simplified image 600 from a scanning electron microscope image of an exemplary embodiment of a non-woven shape memory polymer fabric. The non-woven shape memory fabric comprises a collection of shape memory polymer fibers that are created from bulk polymer source material via a process, such as melt-blowing the polymer, thereby creating a mesh of non-woven shape memory polymer fibers. The shape memory polymer shown was melt-blown from a die onto a collector, thereby creating a non-woven mesh of the collection of shape memory polymer fibers. The particular exemplary embodiment illustrated is embodiment number 8 in the following FIG. 7. The resulting fibers had an average diameter of 5.8 microns (um) and varied in diameter by +/−1.83 microns (95%).

The melt-blown shape memory polymer fabric embodiments included areas of the non-woven shape memory polymer fibers with a varying degree of entanglement per area. The entanglement can also be described as a degree of randomness of fibers, which may vary in each area. Entanglement may include a measure of disorder, randomness, or entropy of the fibers in the areas 606 and 608. For example, the non-woven shape memory polymer fibers in area 606 may differ from the fibers in area 608 in terms of degree of directional randomness, or change in direction of a fiber. As another example, the non-woven shape memory polymer fibers in area 606 may differ from the fibers in area 608 in terms of number of crossings of fibers contained in each unit area. In some areas such as 606 and 608, differently entangled fibers may comprise one or more of the same fiber that is differently formed along the length of the fiber such as in each area. The fibers collected in the melt-blown non-woven mesh generally do not have any directional relationship with either a vertical dimension 602 or a lateral dimension 604 of the non-woven fabric, except as imparted by the rotating collector during the production.

FIG. 7 shows shape memory data for the other exemplary embodiments of non-woven shape memory polymer fabrics. The ranges of processing parameters for the melt-blown embodiments shown used an air pressure of 10-20 pounds per square inch (PSI), feed rate of 0.5-22 meters per minute, and die-collector distance of 95-1000 millimeters (mm). For the first exemplary embodiment of the non-woven fabric, the process resulted in a mean fiber diameter of 9.11 microns (+/−2.03) and a glass transition temperature of 65 degrees centigrade (+/−3.4). For the second exemplary embodiment of the non-woven fabric, the process resulted in a mean fiber diameter of 5.56 microns (+/−2.28) and a glass transition temperature of 65.6 degrees centigrade (+/−2). For the third exemplary embodiment of the non-woven fabric, the process resulted in a mean fiber diameter of 9.06 microns (+/−2.01) and a glass transition temperature of 60.3 degrees centigrade (+/−2.5). For the fourth exemplary embodiment of the non-woven fabric, the process resulted in a mean fiber diameter of 7.89 microns (+/−1.47) and a glass transition temperature of 65 degrees centigrade (+/−2.6). For the fifth exemplary embodiment of the non-woven fabric, the process resulted in a mean fiber diameter of 5.33 microns (+/−1.63) and a glass transition temperature of 63.3 degrees centigrade (+/−4). For the sixth exemplary embodiment of the non-woven fabric, the process resulted in a mean fiber diameter of 5.5 microns (+/−1.62) and a glass transition temperature of 62.6 degrees centigrade (+/−5.1). For the seventh exemplary embodiment, the mean fiber diameter resulted in a mean fiber diameter of 4.09 microns (+/−1.18) and a glass transition temperature of 65 degrees centigrade (+/−4). For the eighth exemplary embodiment of the non-woven fabric, described above, the process resulted in a mean fiber diameter of 5.8 microns (+/−1.83) and a glass transition temperature of 60 degrees centigrade (+/−4.3). For the ninth exemplary embodiment of the non-woven fabric, the process resulted in a mean fiber diameter of 9.07 microns (+/−2.22) and a glass transition temperature of 54.6 degrees centigrade (+/−3.7).

Thus, the ranges achievable with the above processing parameters of an air pressure of 10-20 PSI, a feed rate of 0.5-22 meters per minute, and a die-collector distance of 95-1000 mm, includes a mean fiber diameter of 4-9 microns (+/−2 microns) and a glass transition temperature of 55-65 degrees centigrade (or degrees Celsius) when measured by the peak tan-delta of the modulus measured via a dynamic mechanical analysis (DMA). By varying the processing parameters, advantageous embodiments may be created from with average fiber diameters in the range of 1-10 microns, with similar variances of (+/−2 microns), while maintaining glass transition temperatures in the same ranges described, such as between about 55-65 degrees centigrade (or degrees Celsius). In one embodiment, a glass transition temperature is between 50-70 degrees centigrade, whereas the mean body temperature of the intended animal is below 40 degrees centigrade. The modulus of the resulting fabrics ranged from 20 to 74 MPa, overlapping in range with the modulus range for a supraspinatus tendon of 45-165 MPa.

The fabric may be tuned to create sufficiently slow activation of the shape memory polymer fabric while installed in an animal and exposed to long-term environmental effects of the installation. For example, the composition of a shape memory polymers used for the fabric may be adjusted to decrease water uptake by including hydrophobic polymer components or to raise the glass transition temperature by including different polymer components.

It is clear that many modifications and variations of this embodiment can be made by one skilled in the art without departing from the spirit of the novel art of this disclosure. While specific parameters, including doping, device configurations, parameters of components, and thresholds may have been disclosed, other reference points can also be used. These modifications and variations do not depart from the broader spirit and scope of the present disclosure, and the examples cited here are illustrative rather than limiting.

What is claimed is:

1. A shape memory polymer fabric, comprising:
a collection of non-woven shape memory polymer fibers for orthopedic applications, the collection exhibiting a storage temperature below 40 degrees centigrade, a glass transition temperature at or above 50 degrees centigrade, and a modulus of 20-74 MPa;
wherein the shape memory polymer fabric has a stored strain defining a difference in length of an active dimension of the fabric, the difference in length defining a difference between an installed shape and an unconstrained shape.

2. The shape memory polymer fabric of claim 1, wherein the shape memory polymer fibers have an average fiber diameter between 1 and 10 microns.

3. The shape memory polymer fabric of claim 1, wherein the collection of shape memory polymer fibers form a non-woven mesh with varying degrees of shape memory polymer fiber entanglement.

4. The shape memory polymer fabric of claim 1, wherein the glass transition temperature is determined by a dynamic mechanical analysis technique.

5. The shape memory polymer fabric of claim 1, wherein the glass transition temperature is at or above 60 degrees centigrade.

6. The shape memory polymer fabric of claim 1, wherein the shape memory polymer fabric is configured to have a shape memory response, when exposed to surgical installation inside a human body with an average body temperature at about 37 degrees centigrade without temperature-assisted activation during surgery, the shape memory response comprising activating at an insubstantial rate for a period exceeding 2 months.

7. The shape memory polymer fabric of claim 1, wherein the shape memory polymer fabric comprises a rectangular cross section in the installed shape.

8. The shape memory polymer fabric of claim 1, wherein the shape memory polymer fabric is configured to undergo a monotonic shape memory response to transition between the installed shape and the unconstrained shape.

9. A shape memory polymer fabric, comprising:
a collection of non-woven shape memory polymer fibers for orthopedic applications, the collection exhibiting a storage temperature below 40 degrees centigrade, a glass transition temperature at or above 50 degrees centigrade, a modulus of 20-74 MPa; and
wherein:
the shape memory polymer fabric has a stored strain defining a difference in length of an active dimension of the fabric between an installed shape and an unconstrained shape;
and
the shape memory polymer fabric comprises a rectangular cross section in the installed shape.

* * * * *